United States Patent
Thomason et al.

(10) Patent No.: US 8,790,319 B2
(45) Date of Patent: *Jul. 29, 2014

(54) METHOD AND SYSTEM FOR APPLYING A HEATED SKIN TREATMENT SPRAY

(75) Inventors: Scott Thomason, Macedonia, OH (US); Steven C. Cooper, Athens, GA (US); Charles R. Sweat, Dover, FL (US)

(73) Assignee: Sunless, Inc., Macedonia, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/542,406

(22) Filed: Jul. 5, 2012

(65) Prior Publication Data

US 2013/0018333 A1    Jan. 17, 2013

Related U.S. Application Data

(60) Provisional application No. 61/508,479, filed on Jul. 15, 2011.

(51) Int. Cl.
*B05D 3/04* (2006.01)
*B05C 9/12* (2006.01)
*B05C 9/14* (2006.01)

(52) U.S. Cl.
USPC .......................... 604/290; 427/372.2; 118/58

(58) Field of Classification Search
CPC ...................................................... A61K 6/00
USPC ........................................................ 604/290
See application file for complete search history.

(56) References Cited

U.S. PATENT DOCUMENTS

| | | |
|---|---|---|
| 3,007,178 A | 11/1961 | Altman et al. |
| 3,587,118 A | 6/1971 | Compton |
| 3,596,834 A | 8/1971 | Cushing |
| 3,759,449 A | 9/1973 | Ruthman et al. |
| 3,989,143 A | 11/1976 | Broussard |
| 4,056,078 A | 11/1977 | Blafford et al. |
| 4,130,120 A | 12/1978 | Kohler, Jr. |
| 4,382,424 A | 5/1983 | Altissimo |
| 4,386,739 A | 6/1983 | Kwok |

(Continued)

FOREIGN PATENT DOCUMENTS

| | | |
|---|---|---|
| DE | 3540990 A1 | 5/1987 |
| DE | 3720938 A1 | 1/1989 |

(Continued)

OTHER PUBLICATIONS

"Medicinal Plants". Plant Resources of Tropical Africa: vol. 11. 2008.*

(Continued)

*Primary Examiner* — Leslie Deak
*Assistant Examiner* — Sara Sass
(74) *Attorney, Agent, or Firm* — Venable LLP; Steven J. Schwarz

(57) ABSTRACT

Embodiments disclosed herein propose the controlled application of a heated spray cloud to a target surface. The spray cloud may be delivered in connection with applications of atomized (misted) sunless tanning sprays using a variety of spray systems. A formulation of the cosmetic or conditioning liquid may conduct and retain heat to allow a pleasantly warm spray to be received on the skin surface. The formula may come to temperature quickly and the heat may be retained even though a nozzle cooling effect inherently cools the spray as it leaves the nozzle.

38 Claims, 11 Drawing Sheets

(56) References Cited

U.S. PATENT DOCUMENTS

| | | |
|---|---|---|
| 4,394,967 A | 7/1983 | Amiaut |
| 4,485,503 A | 12/1984 | Rolando et al. |
| 4,523,080 A | 6/1985 | Bolton |
| 4,901,379 A | 2/1990 | Chalberg et al. |
| 5,074,322 A | 12/1991 | Jaw |
| 5,136,735 A | 8/1992 | Zimmerman |
| 5,199,644 A | 4/1993 | Haferkorn |
| 5,228,150 A | 7/1993 | Parker |
| 5,558,276 A | 9/1996 | Barrett et al. |
| 5,864,894 A | 2/1999 | Fedele |
| 5,991,937 A | 11/1999 | Safara |
| 6,117,915 A | 9/2000 | Pereira et al. |
| 6,302,122 B1 | 10/2001 | Parker et al. |
| 6,416,747 B1 | 7/2002 | Laughlin |
| 6,418,573 B1 | 7/2002 | Masuda |
| 6,554,208 B1 | 4/2003 | Venuto, Sr. |
| 6,673,097 B1 | 1/2004 | Venuto, Sr. |
| 7,041,089 B2 | 5/2006 | Laughlin |
| 7,132,010 B2 | 11/2006 | Carlsson |
| 7,387,684 B2 | 6/2008 | Cooper et al. |
| 7,569,037 B1 | 8/2009 | Spivak |
| 2002/0000237 A1 | 1/2002 | Laughlin |
| 2003/0029488 A1 | 2/2003 | Baird |
| 2003/0094510 A1 | 5/2003 | Laughlin |
| 2004/0147884 A1 | 7/2004 | Szurko |
| 2005/0059910 A1 | 3/2005 | Licht et al. |
| 2005/0150467 A1 | 7/2005 | Segura Jobal |
| 2005/0279865 A1 | 12/2005 | Thomason et al. |
| 2006/0064815 A1 | 3/2006 | Guerin et al. |
| 2006/0118039 A1 | 6/2006 | Cooper |
| 2006/0163382 A1 | 7/2006 | Spivak et al. |
| 2006/0207013 A1 | 9/2006 | Deboer et al. |
| 2006/0214027 A1 | 9/2006 | Micheli |
| 2006/0231567 A1 | 10/2006 | Perrone |
| 2006/0275555 A1 | 12/2006 | Colizza et al. |
| 2006/0278661 A1 | 12/2006 | Cooper et al. |
| 2007/0107121 A1 | 5/2007 | Smith et al. |
| 2007/0169261 A1 | 7/2007 | Smith et al. |
| 2007/0197982 A1 | 8/2007 | Thomason et al. |
| 2007/0275021 A1 * | 11/2007 | Lee et al. ............... 424/401 |
| 2008/0237522 A1 | 10/2008 | Morris |
| 2009/0130044 A1 | 5/2009 | Choi et al. |
| 2009/0272316 A1 | 11/2009 | Arnaud et al. |
| 2009/0314857 A1 | 12/2009 | Thomason et al. |
| 2010/0065655 A1 | 3/2010 | Hipperson |
| 2010/0266776 A1 * | 10/2010 | Cooper et al. ............. 427/372.2 |
| 2011/0133004 A1 | 6/2011 | Thomason et al. |
| 2011/0137268 A1 | 6/2011 | Thomason et al. |
| 2011/0259974 A1 | 10/2011 | Cooper et al. |
| 2012/0056017 A1 | 3/2012 | Thomason et al. |
| 2013/0020414 A1 | 1/2013 | Thomason et al. |

FOREIGN PATENT DOCUMENTS

| | | |
|---|---|---|
| WO | WO-2004033107 A2 | 4/2004 |
| WO | WO-2004084983 A1 | 10/2004 |
| WO | WO-2010012903 A1 | 2/2010 |

OTHER PUBLICATIONS

Webster, G., and Rawlings, A. "Basic and Clinical Dermatology: Acne and its Therapy". CRC Press, 2007.*

Ramanathan, M. "Dictionary of Chemistry". Sura Books: 2007.*

Int'l Search Report and Written Opinion for PCT/US2012/046017 mailed Feb. 1, 2013 (10 pages).

Crodafos(tm) CES Data Sheet, "Targeted Delivery Agent for Skin Care," INCI Name*: Cetearyl Alcohol (and) Dicetyl Phosphate (and) Ceteth-10 Phosphate, PN-094R-1, Jan. 28, 2009 (10 pages).

Crodafos(tm) CS20A Data Sheet, Cetearyl Alcohol (and) Ceteth-20 Phosphate, "Primary Emulsifier for Pourable or Sprayable Emulsions," Apr. 14, 2010, DS-156R-7 (9 pages).

Croda Material Safety Data Sheet, Croda Document #CRODA-PRO; SHE-51, Attachment A, Revision Date Dec. 9, 2005 (4 pages).

Crodafos CES Product Brochure, Croda Inc., Feb. 9, 2010 (9 pages).

* cited by examiner

FIG. 2

METHOD AND SYSTEM FOR APPLYING A HEATED SKIN TREATMENT SPRAY

PRIORITY CLAIM

This application claims priority from U.S. Provisional Application for Patent No. 61/508,479, filed Jul. 15, 2011, the disclosure of which is hereby incorporated by reference.

BACKGROUND

Spray devices for the application of liquids onto human skin and hair are well known. Sprays are used for many types of medicines, skin treatments, hair treatments, deodorants, lotions, and cosmetic agents. Specialized automated spray systems are used in tanning salons and spa treatment centers to apply sunless tanning compounds and skin care formulas, such as moisturizers, anti-aging treatments, and exfoliants. The spray solution used for sunless tanning is generally a water-based mixture of DHA (dihydroxyacetone) and/or erythrulose and various other skin care ingredients such as *aloe vera*. Often a cosmetic bronzer is added along with pleasant scents and ingredients to enhance tanning performance, such as formulations to balance skin ph. For best results, the spraying of the solution utilizes a finely atomized spray (mist), as opposed to the use of a spray stream or large spray droplets, because the mist of solution provides for even coverage and reduces the risk of streaking or running of the spray deposit.

The skin treatment spray process has inherently been a cold, uncomfortable experience for the recipient as nozzle expansion effects significantly cool the air and liquid in the spray cloud during application to the skin. Furthermore, cold skin is known to inhibit optimum coverage and performance of the skin care ingredients. Temperatures of the spray cloud can be over 30° F. lower than human body temperature and significantly cooler than ambient temperature (of the liquid or the air emitted from the sprayer).

In salons, customers disrobe for the spray treatment which lasts from 30 seconds to 5 minutes. Some treatments involve sequential spray regimens of alternate ingredients so the experience can be significantly longer. Thus, the length of time the customer is exposed to cold can be significant and may discourage the customer from obtaining the treatment in the first place or returning for an additional treatment at a later date.

Moreover, "goose bumps" or "chill bumps" may form on the skin as an involuntary pilomotor reflex reacting to receiving a cold spray. Applying a spray tanning treatment to skin with chill bumps often produces a poor result. One reason for the poor result is an uneven formation of the chill bumps on certain parts of the body but not on others. For example, chill bumps are more likely to form on a subject's forearm than underneath the arm. Also, chill bumps are more pronounced on a subject's chest than on the subject's stomach; they are also more pronounced on a subject's thighs than on the calves. The resulting tan will be different when a spray tan is applied to a body part with chill bumps than will result when applied to a body part without chill bumps. Often, the resulting tan may have an initial uneven tan color and uneven fading of the tan. The chill bumps may also contribute to increased beading, which is the formation of collected and coalesced droplets of spray tanning solution on the skin and hairs. This beading may cause undesirable "freckling" effects.

A need exists in the art to address the foregoing issues in connection with providing a better skin treatment spray experience and result for the consumer.

Reference is made to Thomason, U.S. Patent Application Publication No. 2005/0279865 (the disclosure of which is hereby incorporated by reference), which teaches a fluid spraying system including a mobile cart that is in fluid communication with a hand held sprayer.

Reference is further made to Venuto, U.S. Pat. No. 6,554,208 (the disclosure of which is hereby incorporated by reference) which teaches a tanning spray booth implementation with a nozzle operable to both spray tanning solution and deliver drying air when not spraying.

Reference is also made to Cooper et al., U.S. Patent Publication No. 2011/0133004 (the disclosure of which is hereby incorporated by reference) which teaches a gantry-type system for spraying a skin treatment solution and a separate heated air stream.

Reference is also made to Cooper et al., U.S. Patent Publication No. 2011/0137268 (the disclosure of which is hereby incorporated by reference) which teaches a hand held skin treatment solution sprayer including a heating element and an supplemental air port.

Reference is also made to Cooper et al., U.S. patent application Ser. No. 13/160,698 (the disclosure of which is hereby incorporated by reference) which teaches a hand held skin treatment solution sprayer having a heating element that heats air emitted in the skin treatment solution spray.

Reference is also made to Pereira et al., U.S. Pat. No. 6,117,915 (the disclosure of which is hereby incorporated by reference) which teaches an oil-in-water emulsifier composition and associated emulsifying waxes, oil-in-water emulsions, and microemulsions that may be used in cosmetic formulations to enhance emulsion stability and oil release.

SUMMARY

Embodiments disclosed herein propose the controlled application of a heated spray cloud in connection with applications of atomized (misted) sunless tanning sprays and other skin-applied sprays using a variety of spray systems. A formulation of the cosmetic or conditioning liquid may allow a pleasantly warm spray to be received on the skin surface. This formulation may include an emulsifying wax, which may be phosphate based. The formulation may also include fatty alcohol and/or oil. The formulation may come to temperature quickly and heat may be retained even though a nozzle cooling effect inherently cools a spray as it leaves a nozzle. This application of a heated tanning spray enhances the efficacy of the tanning compounds and results in a deeper tan color and a longer lasting tan. Furthermore, warm air and warm liquid enhances the spray uniformity result and produces a softer characteristic feel of the spray ingredients on the skin, while reducing complaints of "stickiness" or "tackiness" by the consumer. Deposition efficiency and uniformity of the tan result is also improved.

Spray nozzle systems in a gantry-type and a hand held spray format are presented for applying topical skin treatments, such as sunless tanning formulations, medicines, and lotions. Specifically, a skin treatment spray including an emulsifying wax that retains applied heat is applied to human skin using a hand held or gantry spray system which allows for controlled operation of a heating system and a heated atomizing spray skin treatment solution dispensing system.

A spray nozzle system including an air outlet or outlets positioned near the liquid spray outlet of the spray nozzle to deliver heated air and skin treatment solution including a phosphate based emulsifying wax in the form of a heated spray cloud may improve the atomization of the spray and the comfort and efficacy of the spraying experience. According to certain embodiments, heated air may be applied to atomize or shape the spray cloud that is emitted from the nozzle to increase the spray cloud temperature. In other embodiments, heated air may be delivered through a supplemental air outlet and applied separately but simultaneously with the spray to heat the spray could after it is emitted.

According to one embodiment, a handheld spray device includes at least one air pathway containing a heating element; the air path terminates at an air assisted or an air-atomizing spray nozzle system. The air path may also allow heated air to be delivered through a supplemental air outlet, in addition to, or in lieu of the air being supplied to the nozzle. The nozzle may be of any type of air-assisted nozzle or air-atomizer known in the art, with or without pattern shaping jets, and with or without adjustable porting allowing control of pattern shaping jets. High volume, low pressure (HVLP), low volume, low pressure (LVLP), and adjustable volume, adjustable pressure (AVAP) are types of air atomizing nozzles that may be used with the disclosed spray gun. Other types of spray nozzles may also be used, such as air-assisted, hydraulic, and airbrush nozzles. Spraying systems according to embodiments of the present disclosure may be particularly suited for coating a target surface with a heated skin treatment solution spray because the spray nozzle is capable of producing a well atomized, defined, and shaped spray pattern that is more comfortable on the skin due to its heat retention properties. According to an alternate embodiment, a heating element may be included in a gantry-type sprayer.

The heating element may be positioned upstream of and close to the point of atomization, which provides warmer air and eliminates the disadvantages of a heavy, insulated hose in the event the heating element is located at the source of compressed air. As the heated air flows through the sprayer, it may also heat a thermally conductive liquid tip or channel, which in turn warms the liquid flowing through the channel or tip. The heat may also be used to elevate a liquid temperature in the liquid reservoir. Heated air and/or heated liquid that is emitted from the sprayer may improve spray atomization and create a more comfortable spray tanning experience. Also, warmed liquid flowing through the liquid channels of the sprayer may be less resistant to collection in the liquid channels, which may make the spray gun easier to clean and maintain.

The method of applying a heated spray cloud using the formulation disclosed, has been found to make the experience of skin spray treatments much more comfortable as well as improve coating uniformity. In addition, this method provides an improved tack-free feel of the spray deposit on the skin both during and after the spray session. In the case of sunless tanning with active ingredients such as Erythrulose or DHA (dihydroxyacetone), the system provides for an improved tanning color and increased longevity of the tan.

BRIEF DESCRIPTION OF THE DRAWINGS

A more complete understanding of the invention may be obtained by reference to the following drawings:

FIG. 2 illustrates a graph showing temperature effects on a skin treatment solution spray formulation according to embodiments of the present disclosure;

DETAILED DESCRIPTION OF THE DRAWINGS

Figure 1:
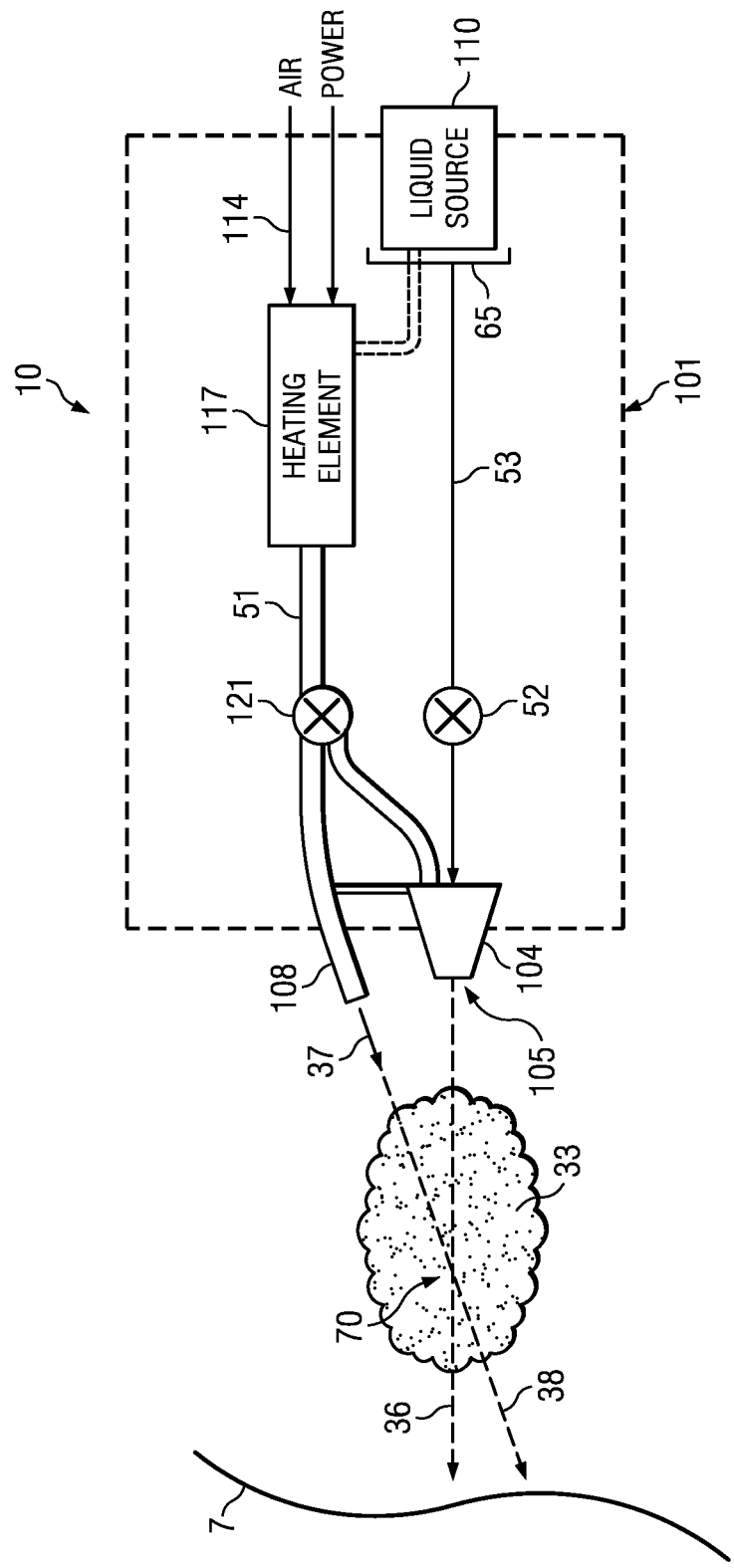
FIG. 1 schematically illustrates a spraying system adapted for use in heating and spraying a skin treatment solution.

Reference is now made to FIG. 1 which schematically illustrates a spraying system 10 adapted for use with a heat retaining formulation of a skin treatment spray. The system 10 is configured to apply an atomized mist of warmed skin treatment spray to a target surface 7 (for example, a customer's skin). The system 10 comprises a hand held, gantry-type, or other suitable spray member (in this case schematically represented by a dotted enclosing line 101, wherein the enclosing line 101 for the spray member generally indicates the use of any suitable enclosure or housing configuration including, for example, a simple structural mount to which spray member components are mounted or a casing which completely encapsulates the spray member components). The line 101 thus generally represents the support, enclosure or housing configuration of the spray member. However, in some embodiments, components of the spraying system 10 that are illustrated inside of the line 101 may be separate and external to the spray member, and components that are illustrated outside of the line 101 may be integral with or enclosed within the spray member, as further described herein.

Supported by the support, enclosure or housing configuration 101 of the spray member is a nozzle 104 that includes a spray jet outlet 105. The spray jet outlet 105 of the nozzle 104 may emit air and liquid from separate orifices to create a finely atomized spray cloud (for example, a mist cloud) 33 of the skin treatment liquid aimed generally in a spray direction 36. The spray mist 33 may be warmed by a supplemental heated air outlet 108 after emission, or the air and/or the liquid emitted by the nozzle 104 may be heated prior to emission.

The nozzle 104 with spray jet outlet 105 may comprise any suitable finely atomizing spray nozzle assembly known to those skilled in the art. For example, the nozzle 104 may comprise any known air-atomizing type atomizing nozzle, such as a high volume, low pressure (HVLP) nozzle, a low volume, low pressure (LVLP) nozzle, or an adjustable volume, adjustable pressure (AVAP) nozzle. In certain embodiments, the nozzle 104 may not be an air-atomizing nozzle, but rather may be a hydraulic nozzle, a sonic nozzle, or any other nozzle that is suitable for creating a spray that may be used for coating a target surface.

In the case of an air-atomizing nozzle, an air source may be used by the nozzle 104 to atomize the spray liquid and form the spray cloud 33 (as well as air used by the nozzle 104 to shape the pattern of the emitted spray cloud). In the case of a mechanical, sonic, or hydraulic atomizer, air may not directly cause the atomization of the spray, but instead may be used for spray delivery, turbulent flow formation, pattern shaping, or directional spray control. According to some non air-atomizing sprayer embodiments, the spray may be created using mechanical, sonic, or hydraulic type atomizers, and air may not be delivered as part of the spray. However, using heated air in connection with the application of a heat retaining skin treatment solution may create a more comfortable and effective spray tanning experience.

The air may be heated by a heating element and/or warmed by a compressor system before reaching the nozzle 104. The nozzle 104 may also include a liquid tip body through which liquid flows. The liquid tip body may be surrounded by an internal heated air stream. In certain embodiments, the nozzle 104 may also support electrostatic spraying of the skin treatment liquid that may have been heated by the internal air stream. In certain other embodiments, heat may be applied directly to the liquid.

Also supported by the support, enclosure or housing configuration 101 is a supplemental heated air outlet 108. The heated air outlet 108 sources a relatively lower pressure heated air stream 37 aimed generally in an air direction 38. The spray direction 36 and air direction 38 are both aimed towards the target surface 7. In a preferred embodiment, the spray direction 36 intersects 70 the air direction 38 such that the air stream 37 mixes with the atomized spray cloud 33 prior to atomized spray cloud 33 contact with the target surface 7. Even more particularly, the air direction 38 is aimed such that the air stream 37 mixes with a leading edge and/or a trailing edge of the atomized spray cloud 33 (in terms of a primary direction of hand held spray member movement when applying the skin treatment liquid to the target surface 7).

In an embodiment, the enclosure or housing configuration 101 of the hand held or gantry spray member may support an air valve 121 coupled in the ducting 51 between the air heating system 117 and the air outlet 108. In other embodiments, the air valve 121 may not be supported by the spray member or the air valve 121 may be eliminated altogether. The air valve 121 at the very least controls the state (on/off) of passage of heated air received from the air heating system 117 to the supplemental heated air outlet 108. In addition, the air valve 121 may further control a rate and/or proportion of flow of heated air received from the air heating system 117 to the heated air outlet 108 and to the nozzle 105. The passed heated air is delivered from the heated air outlet 108 as the heated air stream 37 and/or as air that forms or shapes the spray cloud 33. With respect to controlling the state and rate of flow of heated air, the air valve 121 may comprise any suitably configured controlled air flow valve, and in a preferred implementation, as discussed in more detail herein, may comprise a flap valve adjustment mechanism.

A liquid conduit 53 may be coupled to a liquid source 110 at one end and coupled to the nozzle 104 at another end. The flow of a heat retaining skin treatment liquid may be controlled in certain embodiments by a valve 52, pump, or other liquid flow control device that may be located along the liquid path defined by the ducting of the liquid conduit 53. The liquid tip body may be associated with the nozzle 104, and it may receive the liquid before it is emitted as part of the mist 33. In addition, the liquid tip body may be heated by the heated air flowing through the nozzle 104. The heated liquid tip body may in turn heat the liquid that flows through the liquid tip body. According to an alternate embodiment, the liquid in the liquid conduit 53 may run proximate the heating unit 117 such that the liquid is heated by the heating unit 117 as it flows through the conduit 53. In a further embodiment, the liquid may also be warmed at the liquid source 110 directly by the heat element 117 or by passing heated air into a reservoir holding the liquid. According to non air-atomizing sprayer embodiments, heating the liquid alone may achieve the desired temperature range and subjective warm feeling after receiving the skin treatment solution spray.

In addition to providing a more comfortable feel on the skin, the heated liquid may also flow through the liquid tip body and flow channels more easily. It may also create an improved atomized mist where spray droplets may be a more uniform size. Thus, an improved spray pattern of mist 33 may be received by the target surface 7. In certain embodiments, as explained in greater detail below, the sprayer 101 may include pattern shaping jets, which may be used to create different heated spray patterns.

Further supported by the support, enclosure or housing configuration 101 of the hand held or gantry spray member is an air heating system 117 coupled to supply heated air to the nozzle 104. The air heating system 117 receives air from inlet air ducting 114 and heats the air to a higher temperature than the temperature of the air as received. Any suitable heating element could be used within the air heating system 117. Air heated by the air heating system 117 may flow through main air ducting 51 to the nozzle 104. Depending on the type of nozzle, the heated air may help atomize the mist 33, dry the target surface 7, and the like. Air heated by the air heating system 117 may travel through a separate pattern shaping air duct to nozzle 104. This air may be emitted through a pattern shaping orifice and help shape the pattern of the spray mist 33 to allow it to effectively coat the target surface 7 with the heat retaining skin treatment solution. In certain embodiments, the heated air may also flow through the spray member 101 and through a check valve and heat and/or pressurize liquid in the liquid source 110.

The liquid source 110 may be a container that is filled with the heat retaining skin treatment liquid. Certain oils, emulsifying agents, solids, and waxes may be formulated in the skin treatment solution to improve certain desirable thermal properties that allow the solution to be comfortably received by the subject at an elevated temperature. The elevated temperature of the received skin treatment solution may occur when the solution is sprayed from air-atomizing and non-air atomizing type nozzles, even as the solution cools due to a nozzle expansion effect on the spray as it leaves the nozzle 104. In certain embodiments, the temperature of the received spray may be approximately 99° F., human body temperature. It has been found that spray received comfortably on the skin has a spray cloud temperature within about 10° F. of that of normal skin temperature, 91° F., therefore in the range of 81° to 101° F. The elevated temperature of the received solution may also occur in non-air atomizing nozzles that do not rely on air to create the spray of skin treatment solution. Examples of these types of nozzle include hydraulic and sonic type nozzles. Heating the liquid may allow a warmed spray to be delivered, even as the liquid expands as it is delivered through the non air-atomizing nozzles.

The skin treatment liquid may be a formulation that has a high thermal conductivity and therefore heats quickly. The formulation may also retain this heat such that it remains at an elevated temperature and will be comfortable when sprayed on a subject's skin. These heat retaining properties may be achieved with a sprayable skin treatment solution that includes an emulsifying wax, which may be phosphate-based, particularly ceteth phosphate. This emulsifying wax may contain a blend of fatty alcohol and phosphate esters. According to other embodiments, a variety of emulsifying waxes may be used in the skin treatment spray formulation of the present disclosure. For example, skin treatment spray formulations may include Emulsifying Wax NF, beeswax, plant based or other suitable emulsifying waxes.

The desirable thermal properties include the skin treatment solution's ability to retain heat during three identified phases of the spraying process. The solution should retain heat during the atomization, spray delivery, and deposition phases of the spraying process. Also, receiving the spray solution on the skin may be made more comfortable by reducing the evaporative cooling effects that are felt after the skin spray solution is deposited on the skin. According to certain embodiments, these desirable thermal properties may be affected by the solution's specific heat, thermal conductivity, thermal inertia, thermal diffusivity, and thermal evaporative properties, such as flash point, boiling point, and heat of vaporization.

The skin treatment solution may be a phosphate based emulsifying wax containing a blend of cetearyl alcohol, dicetyl phosphate, and ceteth phosphate in an aqueous base. The blend may be between 1% and 5% by volume. The phosphate based emulsifying wax may be a particular composition called CRODAFOS™ CES or any of that family of phosphate esters that are manufactured and available from Croda, Inc. located in Edison, N.J. This composition primarily includes cetearyl alcohol, dicetyl phosphate, and ceteth phosphate. In certain embodiments, the ceteth phosphate may be ceteth-10 phosphate. The skin treatment solution spray may include the ceteth phosphate composition blended with a sunless tanning compound, such as dihydroxyacetone and/or erythrulose. Other ingredients, such as *aloe vera*, may also be blended to achieve a variety of desirable effects on the skin receiving the spray.

Figure 2:
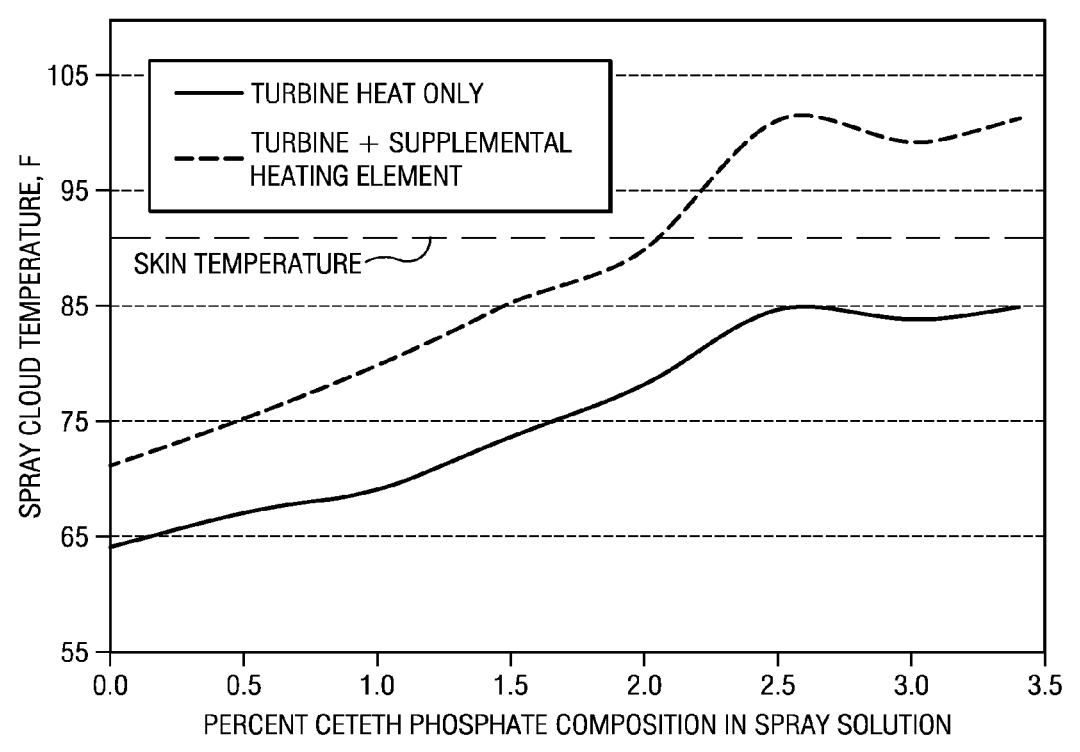

FIG. 2 shows a graph plotting a percentage of the ceteth phosphate composition in the spray solution and a corresponding spray cloud temperature based on different heating methods. As stated above, the ceteth phosphate composition tested included cetearyl alcohol, dicetyl phosphate, and ceteth-10 phosphate. The first heating method was to allow the turbine of the air source to provide the only heat source. The turbine used in the test was capable of raising the temperature of the air at the turbine outlet to approximately 150° Fahrenheit. To increase the temperature of the spray cloud, a 580 watt heater was used to apply additional heat after that heat. This heat was applied closer to the nozzle 105 because the air heated by the turbine cooled as it traveled through a length of hose. The air may be cooled between 20°-30° F. as it flowed through the length of hose. The temperature measurements were taken approximately five inches away from the spray solution emission nozzle.

From FIG. 2 it can be determined that increasing the percentage of ceteth phosphate composition in the skin treatment solution corresponds with an approximately linear increase in spray cloud temperature, which peaks at about 2.5% of ceteth phosphate composition in the spray solution compound. It can also be determined that the 580 Watt supplemental heating element increases the temperature and heats the spray solution such that the spray cloud reaches approximately 99 degrees. Additional power can be used to further increase the spray cloud temperature. Depending on the particular formulation, adding ceteth phosphate composition over a certain percentage may contribute to a slight increase in spray cloud temperature, but it may also result in undesirable attributes of the skin treatment solution, such as increased viscosity inhibiting flow through the sprayer. This percentage has been found to be approximately 2.75% for a ceteth phosphate composition having ceteth-10 phosphate and approximately 6% for a ceteth phosphate composition having a ceteth-20 phosphate.

Figure 3:
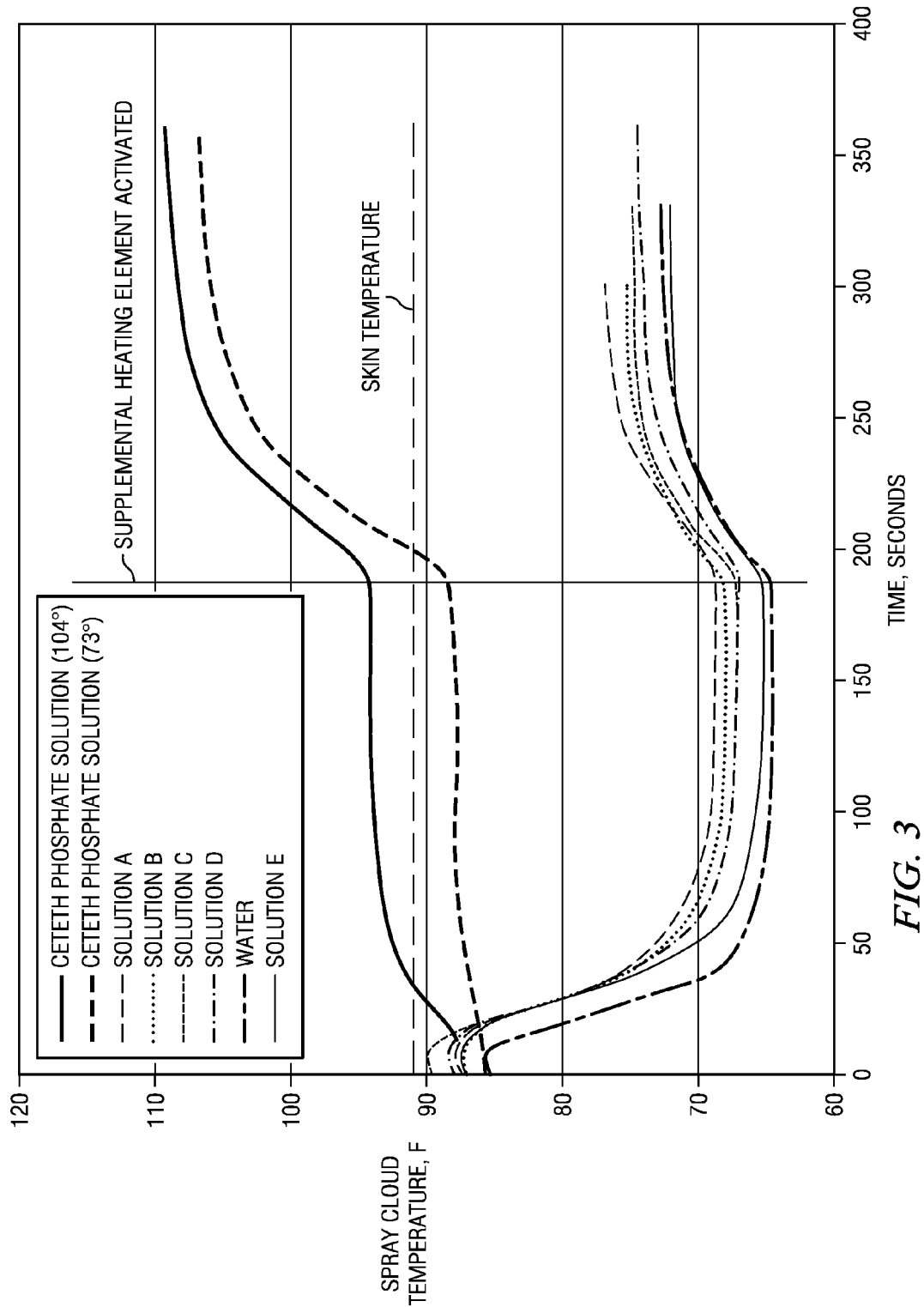
FIG. 3 illustrates a graph of the thermal characteristics of various skin treatment solution sprays.

FIG. 3 is a graph comparing the spray cloud temperatures of various commercially available sprayable sunless tanning skin treatment solutions. The spray temperature of water is also included for comparison purposes. From the graph it can be seen that solutions A-E have spray temperatures that are similar to that of sprayed water, while the solutions that include the ceteth phosphate composition have remarkably different thermal characteristics, particularly the ceteth phosphate composition solution maintains an elevated temperature, as opposed to cooling quickly. Similar to FIG. 2, the test results were obtained using a 140° Fahrenheit pre-heated turbine as the air source. The 140° temperature was measured at the turbine outlet. After three minutes (180 seconds—indicated by the vertical line on the graph), a 580 Watt heating element was activated and the spray cloud was warmed by a supplemental heat source as described above. For the spray skin treatment solution to be comfortable on the skin of the subject, the spray should be elevated above 80° F. and preferably be approximately the same temperature as the body—approximately 99° F. When the ambient temperature is about room temperature (72°-75° F.), the skin temperature measures approximately 91° F., so this is a comfortable spray temperature.

Subjective testing has shown that spray skin solution at 90°-107° F. is the most comfortable temperature range when received on the skin. The preferred embodiment spray heating system should include heat adjustment functionality. In addition, varying amounts of the active ingredients of the ceteth phosphate composition may also allow the desired heat ranges to be achieved. According to certain embodiments, a skin treatment solution containing an emulsifying wax, such as a ceteth phosphate composition, is heated such that it is approximately 20°-30° F. hotter than the ambient temperature when it is emitted as a spray according to the teachings of the present disclosure. Thus, the initial heating of the liquid skin treatment solution and/or the air associated with the spray formation, spray heating, or spray shaping, or spray delivery should account for the inherent nozzle expansion cooling effect associated with air-atomizing and non-air-atomizing spray nozzles. According to the present disclosure, this may be accomplished by applying heat to a particular formulation of skin treatment solution including an emulsifying wax, such as a ceteth phosphate composition.

The solution including the ceteth phosphate composition is graphed at two different initial temperatures. One set of data was taken after preheating the ceteth phosphate composition to approximately 104° F., and the other set of data was recorded with the initial temperature of the liquid skin treatment solution initially at room temperature. Solutions A-E showed a minimal change in the temperature data recorded when they were initially heated to 104° F.

FIG. 3 shows that the spray cloud temperature of the skin treatment solution including a ceteth phosphate composition can be sprayed at significantly higher temperatures and also loses less heat due to nozzle cooling. The graph is based on the temperature of a temperature probe positioned approximately in the center of a spray cloud of the various solutions created by an HVLP nozzle. The time component of the graph predominately shows the time it takes for this probe to come to temperature during the test. When the heating element is activated, the spray cloud temperature of the solution containing the ceteth phosphate composition rises approximately 20°-30° F. and attains a temperature over skin temperature. In contrast, the solutions without the ceteth phosphate composition form significantly cooler HVLP turbine air atomized clouds. When the supplemental heat element is activated, the spray clouds only increase in temperature approximately 5°-10° F. and do not reach human skin temperature. Thus, the ceteth phosphate composition containing solution would feel warm (or at least not cold) when sprayed on the skin with a heated spray system according to the present disclosure, while the solutions without the ceteth phosphate composition would feel cold when sprayed on the skin.

In certain embodiments, the skin treatment solution may include an emulsion containing a blend of fatty alcohol and phosphate esters. In one embodiment, the emulsion may be an oil in water emulsion. The oil may be added to improve the heat transfer, heat retention, and evaporation characteristics of the skin treatment solution. The oil may be synthetic or natural, including botanical oils or oils of any suitable type, such as silicone or dimethicone oil.

There may be two modes of evaporation which may be affected by the oil content of the skin treatment solution. The skin treatment solution may evaporate while it is in transport. That is, the skin treatment solution may evaporate after it is emitted from the nozzle and before it hits the skin surface. Evaporation during transport may contribute to significant cooling of conventional skin treatment solution sprays. Moreover, this evaporation may cause some sprayed droplets to drift such that they are not deposited on the skin. This is due to boundary layer effects on the spray droplets.

Skin treatment solutions according to embodiments of the present disclosure may minimize this evaporation and allow the spray cloud of the skin treatment solution to retain heat and minimize unwanted drifting.

Also, the oil content of the skin treatment solution may affect the evaporation characteristics of the heated skin treatment solution once it is applied to the skin. For example, a certain formulation of oil and skin treatment solution may allow the skin treatment solution to evaporate more slowly, allowing the warm feeling to remain on the subject's skin for a longer period of time. This may be particularly true in comparison to an aqueous solution that does not include oil.

A further consideration of adding oil to affect the rate of evaporation of the skin treatment solution is the sprayed solution's volatility. That is, it is important to maintain an appropriate droplet size of the spray forming the spray cloud. Too large of a droplet size may result in undesirable dripping after the spray is applied to the skin. In the case of cosmetic tanning solution, this dripping may lead to unwanted lines marking the path of the drip that may be left on the subject's skin.

As previously described, consistent with the teaching of the present disclosure, heat may be applied to the skin treatment solution using a variety of techniques. Each of these techniques can be combined with any or all of the others to enhance the heating of the skin treatment solution spray that is ultimately received by the target surface. First, heat may be applied to the liquid component of the heat retaining skin treatment solution in the liquid reservoir and/or the liquid conduit and before it is dispensed by the nozzle. Second, heat may be applied to the air before it is emitted from the nozzle to form the spray cloud. Third, heat may be applied to the emitted spray cloud (which may or may not include heated air and/or heated skin treatment solution) by a supplemental heated air outlet to warm the spray cloud after it has been emitted.

According to the teachings of the present disclosure, it has been found to be beneficial to heat the skin treatment solution and/or air closer to the nozzle before emission. It is also beneficial to heat the solution immediately after emission by heating the spray cloud with warm air.

Another consideration is how well the solution maintains an appropriate consistency to allow it to flow through the liquid conduits and form spray after it has been exposed to a variety of temperatures during shipping or other transport of the bulk solution. For example, a skin treatment solution that has been heated past a certain temperature or cooled past a certain temperature during transport may become too viscous to flow through the liquid conduit and be emitted as a spray. This may be true even if the solution is allowed to return to approximately room temperature before it is used, it still may retain its undesirable viscosity and make it unsprayable.

According to certain embodiments, the liquid source container 110 may be an integral component of, or may be removably mounted to, the support, enclosure or housing configuration 101 of the hand held spray member. The container may be sized to store a relatively small amount of skin treatment liquid (for example, one or a few doses selected for each spray session or application). The container may be received by a receptacle 65 formed in the support, enclosure or housing configuration 101 of the hand held spray member and coupled to the liquid channel 53. In an alternative configuration, the container may instead comprise an external tank configuration storing the skin treatment liquid and coupled to the liquid channel 53 using a hose.

The reference to a liquid source 110 includes the supply of heat retaining skin treatment solution comprising an emulsifying wax. The liquid source 110 may be a single liquid tank supplying a single type (or container) of liquid for spray application as well as the use of multiple liquid tanks (or containers) each containing a distinct liquid for customer selection and skin application. When multiple tanks are provided, the customer can design a multi-product spray session.

The heating element 117 may receive power from a power supply that is either internal or external to the hand held or gantry spray member. The heating element 117 can be incorporated directly into inlet air ducting 114 and/or into the liquid channel 53 and/or the liquid source 110. According to certain embodiments, as discussed in more detail herein, the heating element 117 for a hand held sprayer may be positioned in a handle of the hand held spray member. For a gantry type sprayer, the heating element 117 may be placed in close proximity to the nozzle 105 to reduce cooling as the liquid or air flows between the heating element 117 and the nozzle 105.

Air supplied to inlet air ducting 114 may be ambient air from an air source. The air source may be a compressed air source that may incorporate a fan, a blower or a compressor that may be external or internal to the hand held spray member 101. The compressor of the air supply may be any suitable air moving device, such as a fan, blower, turbine, or piston, rotary or diaphragm compressor, or other air pump.

Air from the air source flows to the air heating system 117, which then heats the received air as it passes to the nozzle 104 or the supplemental air outlet 108. In certain embodiments, the air source may itself increase the temperature of the air slightly. With this temperature increase, a lower rated heating system may be used. In any event, the air received by the nozzle 104 is warmer than the ambient air temperature (i.e., warmer than the air temperature where the target 7 is located).

Figure 4A:
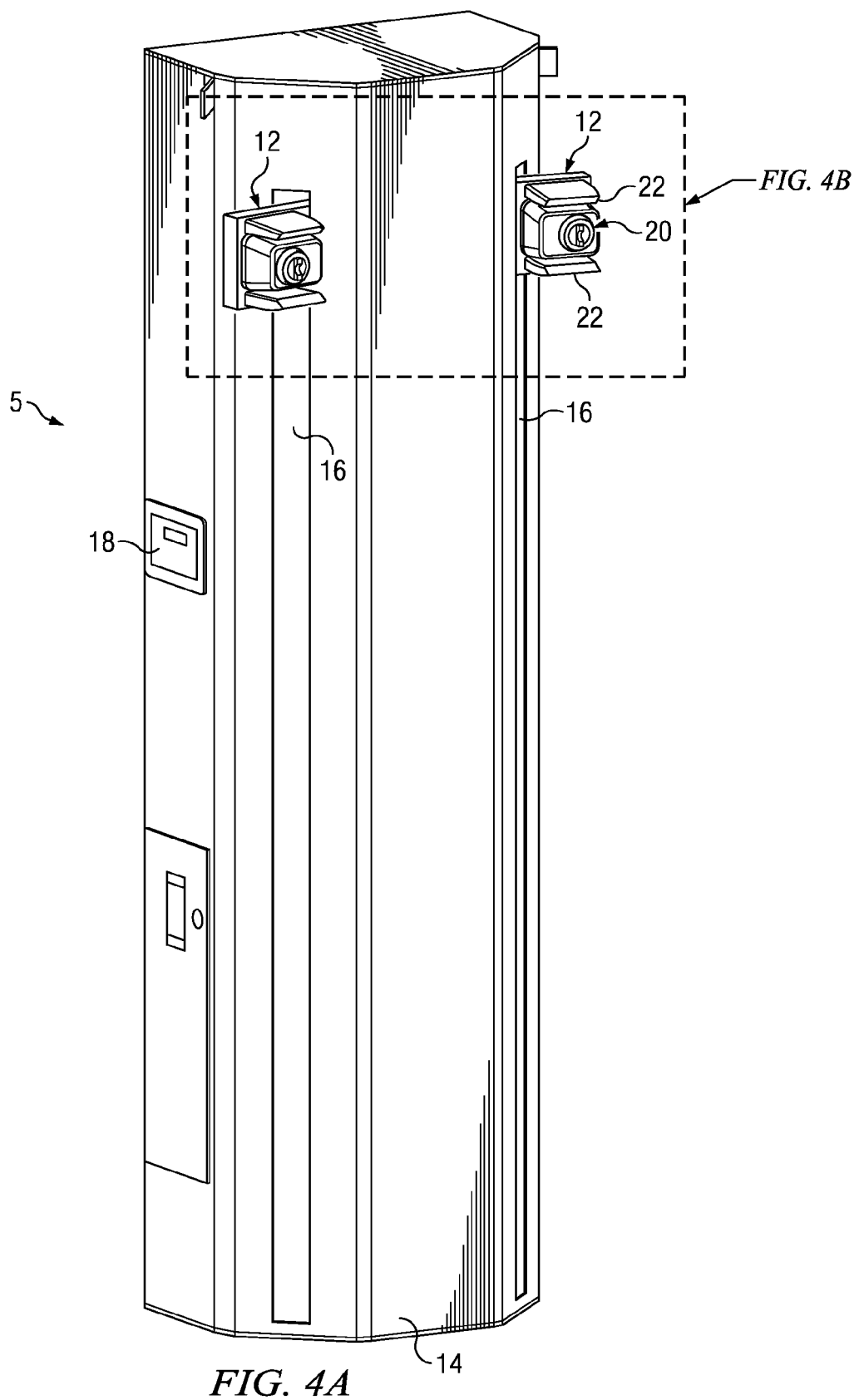
FIGS. 4A and 4B illustrate a spray gantry adapted for use in heating and spraying a skin treatment solution.
Figure 4B:
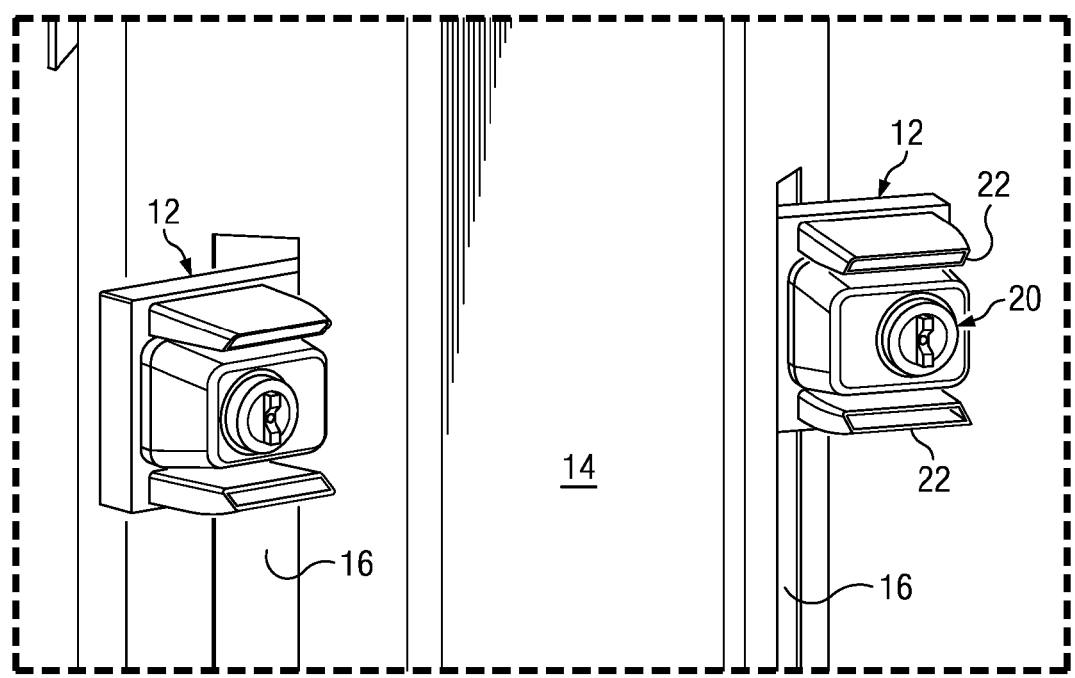

FIGS. 4A and 4B illustrate an automatic system 5 for spraying skin treatment solutions that are heated and retain heat such that they feel comfortable and not cold when coming in contact with a subject's skin. The system 5 comprises one or more sprayers 12 installed on a gantry 14 that is configured to move the sprayer 12 in at least one direction. According to the teaching of the present disclosure, the sprayer 12 may include a nozzle 20 that delivers a spray of heat retaining skin treatment solution. The emitted spray may or may not have been heated before emission. In either case, the spray cloud may then be heated by warm air delivered by one or more air outlets 22 that are separate from the air of the nozzle 20.

In one embodiment, the gantry 14 is configured with a mechanism to traverse each sprayer 12 along a linear guide track 16 having a vertical orientation. In another implementation, the sprayer 20 is installed on a gantry including a multi-axis robotic guide mechanism configured to move the nozzle in at least one linear direction (for example, vertical) and may further support movement in another linear direction (such as, for example, horizontal). In another implementation, the sprayer 12 is installed on gantry including a pivot mechanism to support change in the angular orientation of the spray direction (for example, vertical and/or horizontal).

Combinations of the foregoing movement mechanisms may be employed by the gantry if desired. A control panel 18 is coupled to a control system which controls gantry operation to move the sprayers 12 (for example, along the linear guide track 16, or in any supported linear direction or angular orientation). Each sprayer 12 is mounted to the gantry and includes a nozzle 20 (or multiple nozzles 20) and low pressure supplemental air outlet 22 (or multiple low pressure air outlets 22). The control system further controls actuation of each sprayer 12 to output from the one or more nozzles 20 a spray jet containing a heat retaining skin treatment solution. The control system may further control actuation of each sprayer 12 to output from the one or more air outlets 22 a stream of heated air flow (which is supplemental to any high pressure air used at the nozzle 20 for atomization and/or pattern shaping, which may or may not have been heated). The supplemental air outlets 22 for providing heated air are shown positioned both above and below the nozzle 20 on each sprayer 12, although it will be understood that only a single air outlet 22 (adjacent the nozzle 20) is necessary. A heating element (reference number 117, FIG. 1) is provided to heat the air and/or liquid delivered to and output from the heated air outlet 22.

In one embodiment, the spray from the nozzle 20 may be controlled separately from the air flow from heated air outlet 22 to allow a sequence of operations to be performed in connection with the spraying heat retaining skin treatment, such as pre-warming of the skin, followed by separate spraying and drying cycles. The heated air flow from the air outlets 22 positioned above and below the spray outlet 20 is provided in a controlled manner for a number of purposes: to pre-warm the skin, to warm both the leading and trailing edges of the spray jet (i.e., the spray cloud) as the jet is naturally bent due to movement of the sprayer 12 along the guide track 16, and to provide a drying air stream after the spray cloud passes (or independent of spray cloud application).

In an alternate embodiment of a gantry spray system, the nozzle 20 may move along the gantry while a supplemental air outlet remains fixed adjacent the guide track. An example of this embodiment is described in U.S. Patent Application Publication 2010/0266776, which is hereby incorporated by reference.

The movement among and between modes is designed to enhance the consumer's skin treatment spray experience and improve the result, such as an improved spray tan. Warm air from the air drying outlet serves to prepare the skin for treatment, warm the skin for customer comfort, and dry the skin evenly after application. Alternating between spray application and warm air application improves the tanning result. Furthermore, the mixing relatively low pressure warm air application in with liquid spraying (i.e., mixing into the spray cloud) reduces the discomfort experienced by the consumer due temperature drop of the spray liquid resulting from high pressure nozzle expansion effects.

Although an air atomizing nozzle is shown in FIGS. 4A and 4B, it will be understood that a suitable hydraulic nozzle, sonic or other type nozzle could alternatively be used. In the case of an air-atomizing nozzle, either a single air source or separate air sources may be used for the heated air (as supplemental air) and the atomizing and/or pattern shaping air used by the air-assisted nozzle. In the case of an air-assisted high volume, low pressure (HVLP) nozzle, the turbine itself can be used as a heated air source; conduits can be ported to provide air at a higher pressure for atomization and pattern shaping, and provide heated air at a lower pressure for warming the emitted spray cloud. Additionally, one or more heating elements can be incorporated directly into a liquid conduit, a liquid reservoir, an air conduit or at the exit of a supplemental air outlet.

Figure 5A:
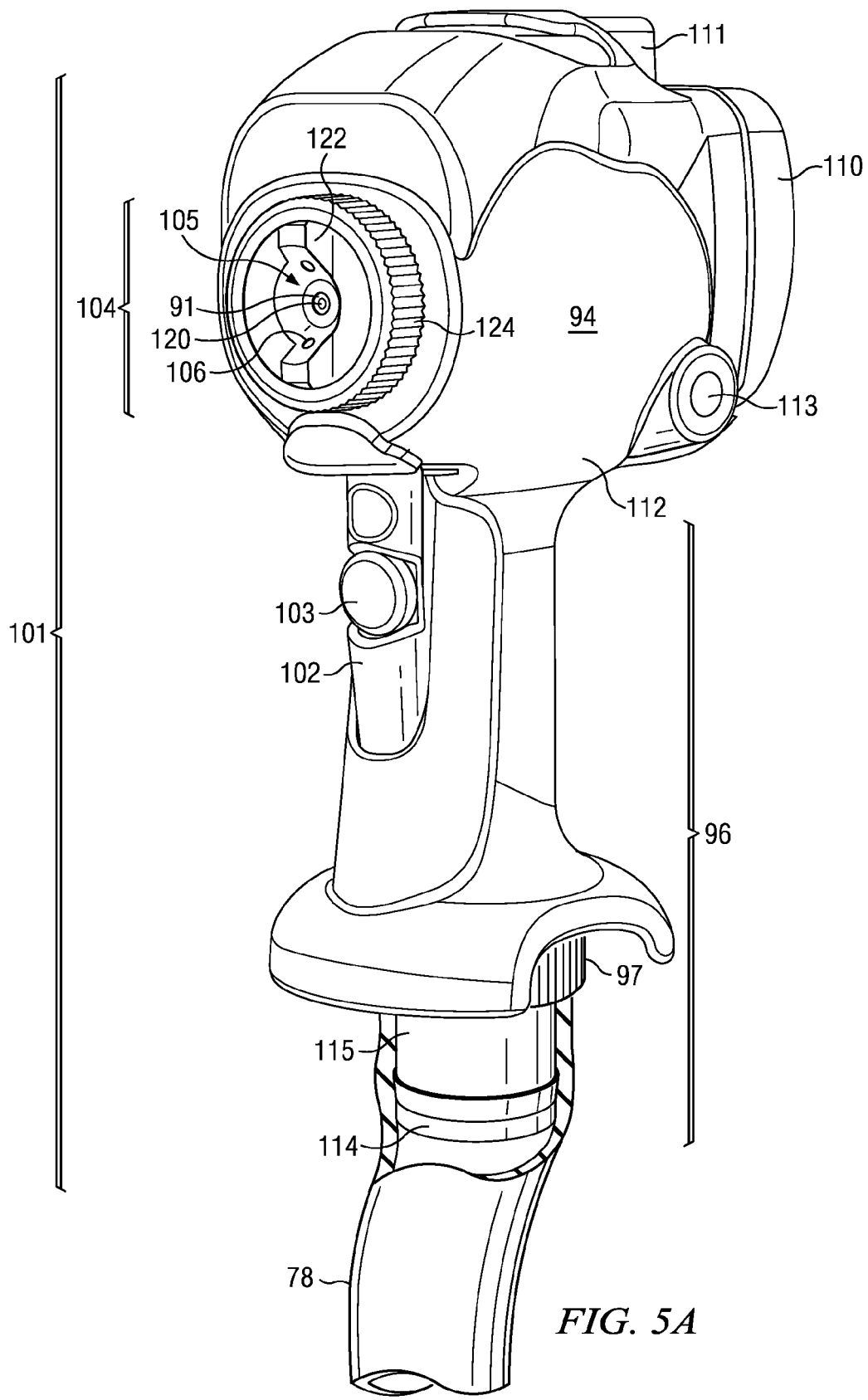
FIGS. 5A and 5B show an exemplary implementation of a sprayer of the type shown in FIG. 1.
Figure 5B:
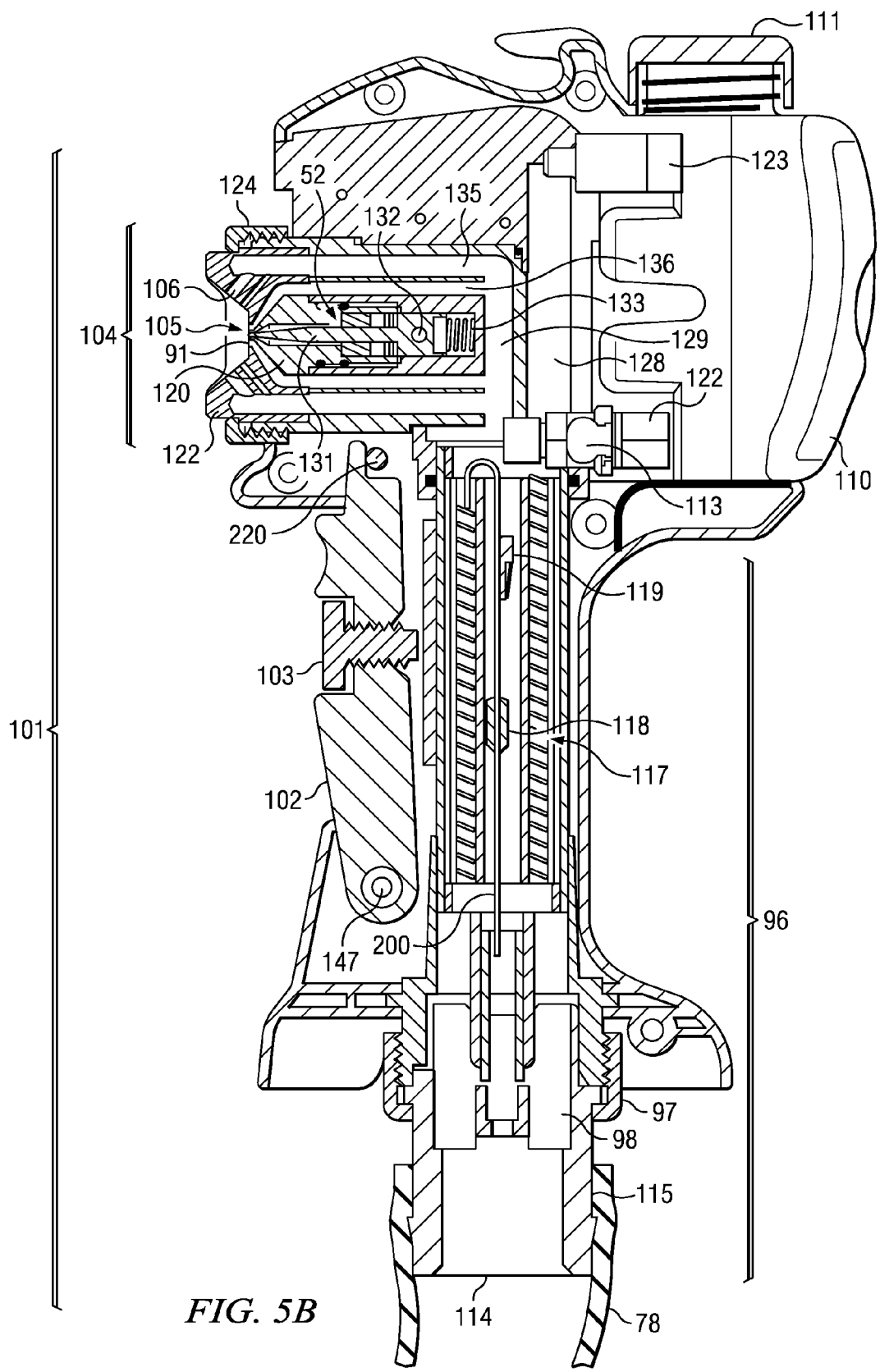

Reference is now made to FIGS. 5A and 5B, which illustrate an exemplary implementation of a hand held sprayer implementing the schematic representation for delivering a heated skin treatment spray to a target surface, as shown in FIG. 1. The support, enclosure or housing configuration 101 of the hand held spray member implementation includes a suitably sized and shaped housing (or shroud) 112 for containing the nozzle 104, ducting for air and liquid flow, control device 52 for controlling liquid flow, air heating system 117, and a trigger-type 102 actuator for controlling operation of the hand held spray member. In an exemplary configuration, the housing 112 includes a barrel shaped portion 94 and a handle shaped portion 96. The spray member 101 may be configured to receive and connect to a hose 78. The hose 78 may run from the air source to a fitting on spray member 101. The hose 78 may be a conduit that carries air and/or liquid to spray member 101, where it may be converted into spray mist 33.

The front of the enclosure or housing configuration 101 of the hand held spray member implementation shows the spray nozzle 104 of the air atomizing type with the spray jet outlet 105 and mist shaping air ports 106 provided immediately adjacent the spray jet outlet 105. According to certain embodiments, the spray jet outlet 105 may include a liquid tip body 120 and an atomizing air port 91 that annularly surrounds and is concentric with the liquid tip body 120. Concentric liquid and air ports may be particularly suited for spray applications used to coat a target surface 7. The mist shaping air ports 106 supply air used by the nozzle 104 for pattern shaping of the spray cloud, for example, to shape the spray cloud into a flat fan-like spray shape, which may allow greater spray coverage of the target surface. In other embodiments, the spray cloud may be shaped to form a pinpoint spray pattern, which may allow more spray to coat a smaller portion of the target surface.

In certain embodiments, adjustable porting may allow additional control over the mist shaping air. A port size may be adjusted by rotating an air cap to a position that blocks air from escaping through a portion of the pattern shaping ports 106. This blockage will cause higher pressure air through the atomizing port 91 or other heated air emitting orifices. Adjusting porting may allow the atomizing air port 91 to supply relatively higher pressure air used by the nozzle 104 for atomization of the spray liquid to create the spray cloud. This air pressure may be higher than the air pressure used for pattern shaping. The air pressure in the nozzle may be less than in conventional liquid spray systems such that less heat of the pressurized air may be lost due to expansion as it leaves the nozzle 104. In certain embodiments, the pressure may be less than 10 psi.

Air flow ports and outlets may be enlarged to reduce the expansion cooling effect on the heated air. The volumetric flow rate for the heated air emitted by the nozzle 104 and the air port 91 may be in the range of 3 to 50 standard cubic feet per minute (SCFM). The air pressure may be between 0.3 to 30 pounds per square inch (psi). In order to minimize heat loss due to expansion, the air pressure at the nozzle 104 may be limited to less than 5 psi. In certain embodiments, the nozzle pressure may be between 0.2 and 1 psi.

According to the illustrated embodiment, the nozzle 104 includes an air cap 122 that is secured to the hand held sprayer 101 by a spray jet retaining ring 124. The air cap 122 may be made of any suitable material. In certain embodiments, it may be metal or plastic. The air cap may channel heated air to the atomizing air ports 91 and the pattern shaping air ports 106.

The liquid source 110 is attachable to a rear of the barrel portion 94 of the sprayer. The liquid source 110 comprises a single liquid tank supplying skin treatment solution formulated to conduct and retain heat as described above. The tank may be filled through a cap 111. The container forming the liquid source 110 is also detachable through actuation of a mechanical release button 113. This allows the user to change the type of spray liquid being applied by changing liquid containers. According to certain embodiments, the location of the tank may be such that liquid is heated by conduction through the walls of the tank.

The inlet air ducting 114 is provided at a base of the handle portion 96. Tubular member 115 supports connection of the air hose 78 to the hand held sprayer 101 using the retention ring 97. The sprayer 101 also includes an external trigger 102. The limit of trigger 102 actuation may be controlled by a set screw 103.

Reference is now made to FIG. 5B, which illustrates a cross sectional view of the hand held sprayer shown in FIG. 5A. The nozzle 104 used in this implementation is of an HVLP type, but could comprise any air-assisted nozzle having an air flow and creating the spray cloud. Liquid for spraying is passed from liquid valve 52 by internal ducting to the nozzle spray jet outlet 105 where it is atomized in response to the air supplied at the atomizing air port 91 to form the atomized spray cloud and pattern shaped in response to the air supplied at the air ports 106 so as to shape the atomized spray cloud (for example, into a fan-like pattern). Heated air is passed by internal ducting and distributed among and between the air ports 91 and 106.

In an alternative configuration, the air ports 106 may be configured to not only shape the atomized spray cloud but also to provide heated air for purposes of warming the spray cloud. To implement this configuration, the internal ducting of the nozzle 104 may be configured so that the pattern shaping air ports 106 receive the heated air. Additionally, the pattern shaping air ports 106 may be designed to be low pressure outlets that minimize a nozzle cooling effect on the spray cloud.

Air is communicated through the hose 78 and received at the inlet air ducting 114 at the base of the handle portion 96. The received air passes up through the handle portion 96. The air heating system 117 may be located at various locations in the hand held sprayer 101. For example, the heating system 117 may be installed in the handle portion 96 within the ducting carrying the air received at inlet ducting 114. The hose 78 may thread into the tubular member 115 and be further secured to the handle portion 96 using the retaining ring 97. In other embodiments, the heating element 117 may be located in the hose 78 and/or in the tubular member 115 proximate the hose end that connects to the hand held spray member 101. In this embodiment, the hose 78 including the heating element 117 may be detachable such that the heating element 117 may be removed from the spray member 101. Regardless whether the heating element 117 is removable or non-removable from the spray member 101, locating the heating element 117 near the spray member end of the hose 78 may facilitate heat retention because heated air is not required to flow through a significant length of hose 78, such that considerable heat is lost. According to certain embodiments, the air may cool between 20°-30° F. travelling through a length of hose. In certain embodiments, the hose 78 may also carry the wires to make an electrical connection between the power source and the spray member 101. In this embodiment, an electrical connector 98 may be located within the handle portion 96. However, if the heating element 117 is removable with the hose 78, then it may not be necessary to have an electrical connection between the hose 78 and the hand held spray member 101.

As described above, the heating system 117 includes a thermal sensor that may be in the form of a thermal fuse 118 and/or a thermal switch 119 (in the form, for example, of a thermostat) functioning as safety devices with respect to sprayer operation so as to protect against an overheating or malfunctioning situation. A perspective, partially broken away view of the heating system 117 is shown in FIG. 7A. A longitudinal cross-section is shown in FIG. 7B. A lateral cross-section is shown in FIG. 7C. Power to the heating system 117 is supplied by power lines 200. The heating system 117 includes a cylindrical tube support 202. The cylindrical tube support 202 may be made from an electrically and thermally insulating material such as Garolite or other suitable fiberglass composite or plastic material. A ceramic core 204 is installed within the tube support 202. A mica wrap 206 is positioned between the inner surface of the tube support 202 and the outer periphery of the ceramic core 204. The ceramic core 204 is formed to include a central longitudinal channel 208 and a plurality of peripheral longitudinal channels 210. These channels 208 and 210 are sized to permit the flow of air through the heating system 117. The power lines 200 pass through the central longitudinal channel 208, and the thermal fuse 118 and thermal switch 119 are installed within the central longitudinal channel 208. A coiled resistance wire 212 is installed within each one of the peripheral longitudinal channels 210. The coiled resistance wires 212 are electrically connected to each other and to the power lines 200.

The heating system 117 is designed to quickly ramp up to a desired air heating temperature and maintain that temperature over the course of a spray session. In addition, if the heating system 117 gets too hot (for example if there is no air flowing through the heating system 117), the thermal switch 119 may operate to interrupt the power to the heating system 117 to control temperatures and to prevent a dangerous overheating condition. The thermal switch 119 may be a resettable thermal switch. As such, the thermal switch 119 may interrupt the power substantially immediately. The heating system 117 may have as input an analog or digital signal from a thermal sensor that allows the temperature of the heating system 117 to be modulated, as opposed to mechanically interrupting power to it.

Reference is once again made to FIG. 5B. After passing through the heating system 117, the air (now heated air) passes through internal ducting and is made available within the hand held sprayer 101 for a number of purposes. First, the heated air is delivered to an air channel 128, which, in certain embodiments may be coupled through an inlet check valve 123 to the liquid supply 110 container. The check valve 123 only permits air to enter the liquid supply 110 container, and thus the air supplied from the air channel 128 functions to pressurize and heat the liquid supply 110 container. In other embodiments, the liquid supply 110 may not be pressurized by the heated air. For example, in one embodiment the liquid supply 110 may be external to the hand held spray member, and the heated air may not reach the liquid supply 110.

Second, the heated air is delivered to a nozzle air channel 129. In certain embodiments, the nozzle air channel 129 may be separate from the air channel 128. This nozzle air channel 129 is coupled to the pattern shaping air ports 106 through pattern shaping air channel 135. Thus, heated pattern shaping air is supplied to the pattern shaping air ports 106 of the nozzle 104. This nozzle air channel 129 is further coupled to the air atomization ports 91 through atomization air channel 136. Thus, heated atomizing air is also supplied to the air atomization air ports 91 at the spray jet outlet 105 of the nozzle 104. One or more air valves (not explicitly shown) may be used to control heated air delivery and the air pressure to the atomizing air port 91 and the pattern shaping air ports 106.

Heating of the heat retaining skin treatment formulation may occur as the atomization air channel 136 receives heated air from the heating system 117 through the nozzle air channel 129, the heated air will also heat the liquid tip body 120 and liquid conduit as the heated air flows to the atomizing air ports 91. This heated liquid tip body 120 may transfer heat to the liquid as it flows to spray jet outlet 105. The liquid tip body 120 may be metal or other material that effectively conducts heat. In one embodiment, the liquid tip body 120 may be stainless steel.

Heated air exiting from the air atomization port 91 may assist atomization of the liquid provided from the liquid supply 110 container and passing through the quick connect valve 122 and internal ducting to the nozzle spray jet outlet 105 to form the spray cloud 33. In certain embodiments, the air pressure may be reduced such that the spray mist remains warm. For example, air pressure below 10 p.s.i. may create an effective spray mist and reduce the amount of heat loss due to expansion of the air as it exits the atomizing air port 91. In certain embodiments, nozzle geometry in connection with the heat retaining skin treatment solution described herein may reduce heated air cooling due to rapid air expansion at the nozzle 104. Corresponding to the reduced air pressure, the flow rate of the liquid may also be reduced to allow for atomization of a lesser quantity of liquid to ensure that all of the liquid ejected from the spray jet outlet 105 is atomized.

The heat conducting and heat retaining skin treatment liquid for the spraying operation is sourced from the liquid supply 110 container. The liquid in the liquid supply 110 container is coupled through an outlet quick connect valve 122 through internal ducting (not explicitly shown) to the nozzle spray jet outlet 105. The outlet quick connect valve 122 for the liquid supply 110 container in this implementation does not function to control the state or rate of liquid flow or the size of the atomized spray cloud. Rather, a separate liquid flow control device or liquid valve 52 is provided in the nozzle 104. This liquid control valve 52 in the illustrated configuration comprises a needle valve (to be described) associated with the nozzle jet outlet 105. In other embodiments, the flow of liquid may be controlled by a pump, a remote solenoid valve, or a pneumatically controlled valve. The liquid flow control device may be internal to the hand held spray member 101 or may remote to the spray member 101. Also, the rate of flow of the liquid may be regulated by controlling air pressure into the liquid supply container 110 at inlet check valve 123.

When the liquid control valve 52 is closed, the flow of liquid from the liquid supply 110 container to the nozzle spray jet outlet 105 is blocked and only heated air may be delivered by the nozzle 104. As the liquid control valve 52 opens, liquid from the liquid supply 110 container flows to nozzle spray jet outlet 105. This flow may be assisted because the liquid supply 110 container has been pressurized by heated air passing into the liquid supply 110 container through the inlet check valve 123. In a non-needle valve implementation, the outlet check valve 122 may be configured to implement the functionality of the liquid control valve 52 (for example through controlling suction of liquid from the liquid supply 110 container to nozzle spray jet outlet 105).

In the needle valve configuration, the needle valve comprises a liquid flow needle 131 for the liquid control valve 52 that is biased by a spring 133 in a closed position that shuts off the flow of liquid to the nozzle spray jet outlet 105. The liquid flow needle 131 moves within the nozzle 104 in response to actuation of a pin 132. When the trigger 102 is actuated, the trigger mechanism rotates about the pivot 147 and engages the pin 220. Movement of the pin 220 (in response to the trigger 102 actuation) causes the control linkage mechanism to move the needle valve pin 132 and open the liquid control valve 52 by moving the liquid flow needle 131 within the nozzle 104. When the trigger 102 is in a fully released position, the control linkage mechanism (along with spring 133) sets the fluid flow needle 131 of liquid control valve 52 into a fully closed. As the trigger 102 is further actuated, the control linkage mechanism begins to open the needle valve. When the trigger 102 moves towards the fully actuated position, the control linkage mechanism sets the liquid flow needle 131 into a position where the liquid control valve 52 is fully open. The set screw 103 provides a mechanism for controlling the maximum degree of trigger 102 actuation and thus can limit the degree of opening the liquid control valve 52 in response to full actuation of the trigger 102.

Figure 6A:
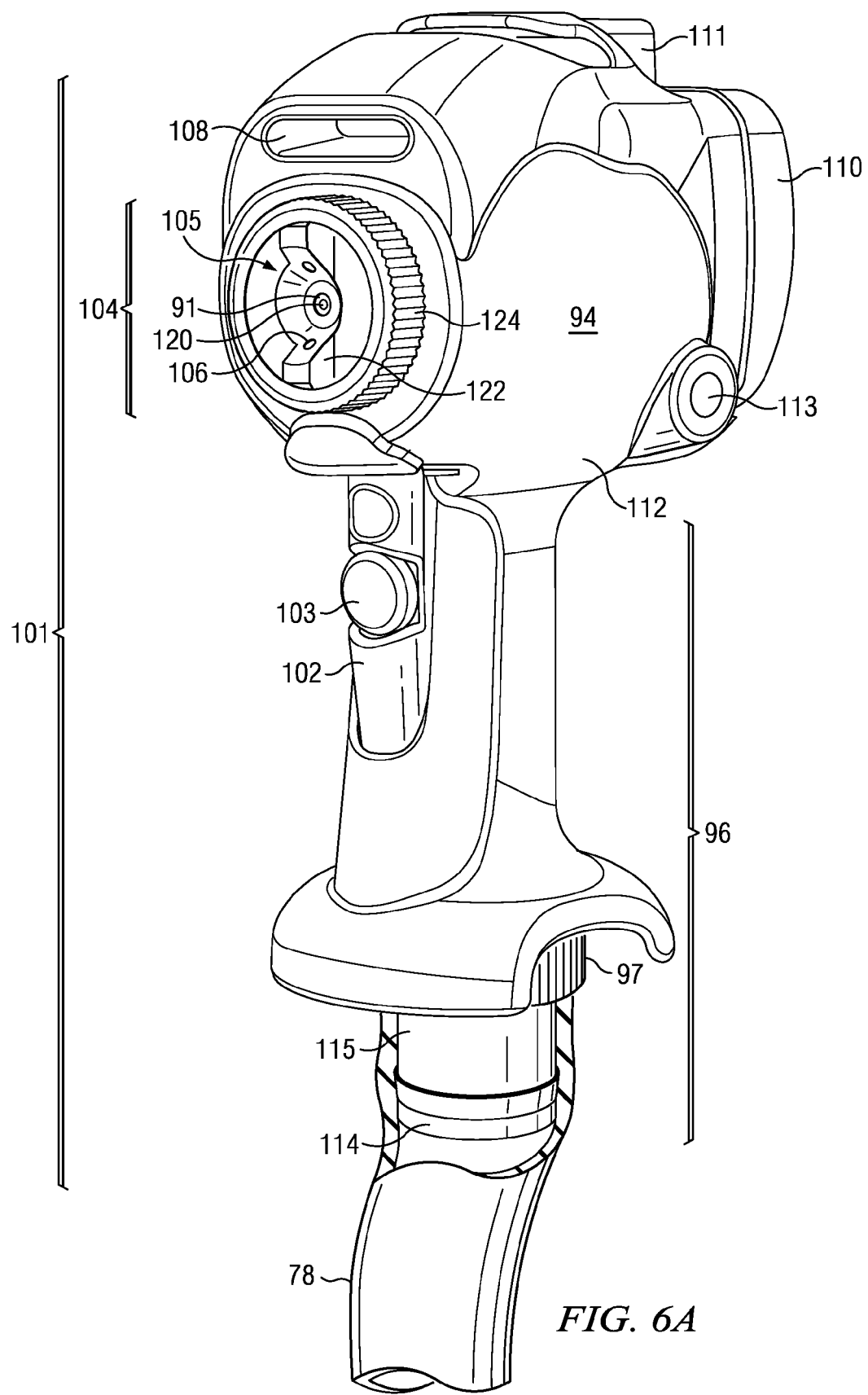
FIGS. 6A and 6B show an exemplary implementation of a sprayer of the type shown in FIG. 1 and including a supplemental air outlet.
Figure 6B:
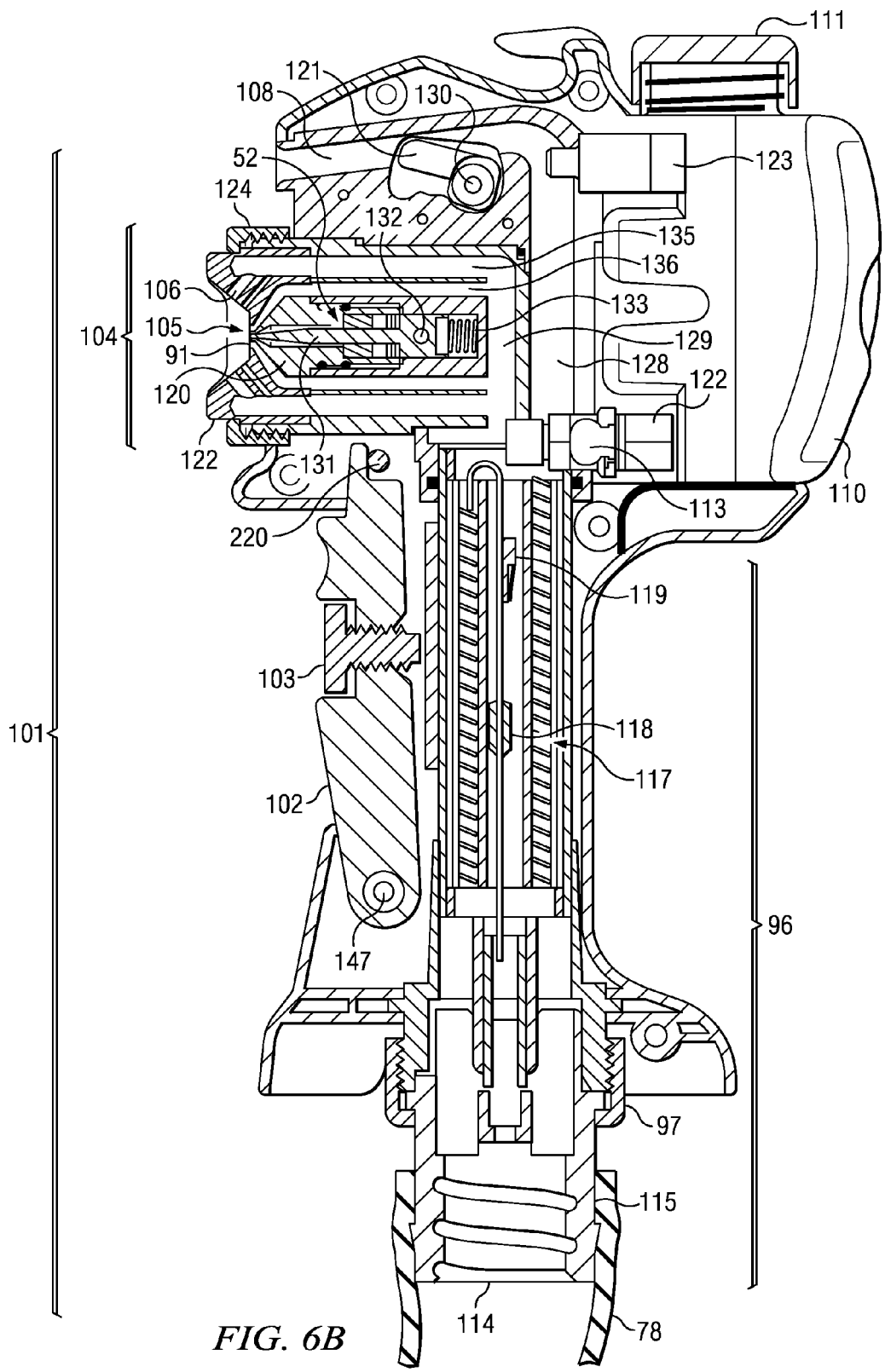
Figure 7A:
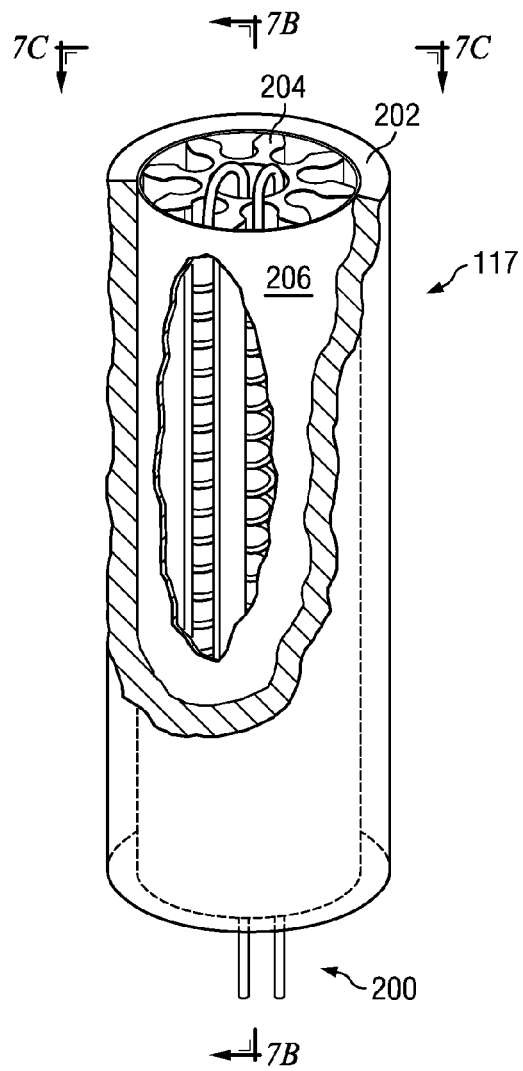
FIGS. 7A to 7C illustrate various views of a heating element used within the hand held sprayer or automatic gantry sprayer of the present disclosure.
Figure 7B:
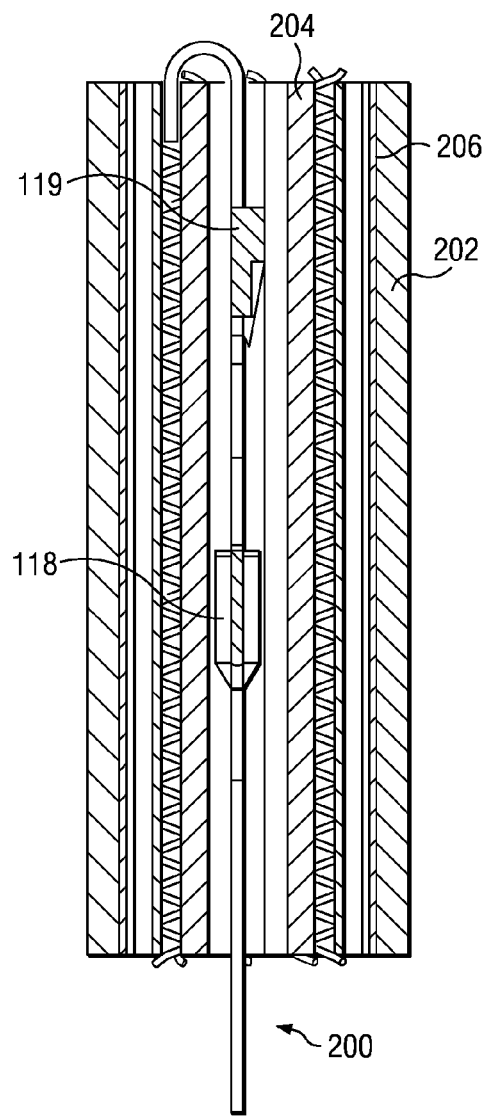
Figure 7C:
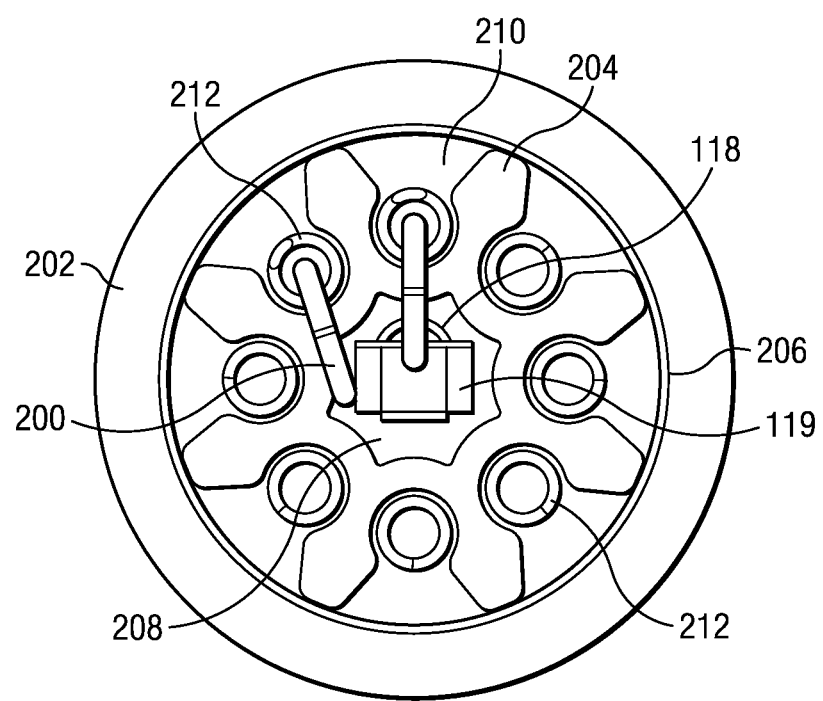

FIGS. 6A and 6B illustrate an embodiment of the hand held sprayer similar to that shown in FIGS. 5A and 5B and having a supplemental air outlet 108 and a supplemental air valve 130. Activating the supplemental air valve 130 allows heated air to be delivered by supplemental air outlet 108. This heated air can be used to warm the spray cloud of heat retaining skin treatment solution emitted from the nozzle 104. The spray cloud may or may not have been heated before being emitted.

The system 10 described herein supports exercising control over the operation of the heated air flow, heat levels, nozzle operation, liquid selection, and nozzle movement. Improved results using the apparatus and process described herein, with a trial using DHA (dihydroxyacetone) based sunless tanning compounds, include:

Increases tan color by allowing higher quantities of sprayed active ingredient to be deposited due to a layering process where the heated spray is applied; the skin is re-dried quickly by the warm air before another spray pass over the same target area;

Promotes improved efficacy and quicker activity of DHA by drying the top layer of the stratum corneum skin layer; this results in more uniform and longer lasting tan color with more even fading characteristics;

Opens skin surface pores to allow for better penetration of tanning compound and skin care ingredients;

Reduces the occurrence of chill bumps on the skin that may result in an uneven and poor quality tan;

Properly controlled heated air dries the skin of any perspiration or other moisture, including the water based spray itself, that may cause an uneven tanning effect and limit DHA efficacy;

Prevents dripping or streaking of the sprayed material during the tanning process which can cause an uneven tanning result;

Reduces overspray by reducing spray evaporation during transport;

Reduces evaporative cooling effects felt on the skin;

Reduces cooling during spray cloud transport by altering the evaporative effects; and Eliminates the step of drying the skin off with a towel which causes partial removal and disturbance of the evenly deposited layer from the spray application.

Although preferred embodiments of the method and apparatus of the present invention have been illustrated in the accompanying Drawings and described in the foregoing Detailed Description, it will be understood that the invention is not limited to the embodiments disclosed, but is capable of numerous rearrangements, modifications and substitutions without departing from the spirit of the invention as set forth and defined by the following claims.

The invention claimed is:

1. A method for applying a heated skin treatment spray to coat a target surface, comprising: heating a heat retaining emulsifying wax;
emitting a heat retaining skin treatment solution comprising the heat retaining emulsifying wax;
atomizing the heat retaining skin treatment solution using an atomizing nozzle associated with a sprayer to create a spray cloud;
wherein heating the heat retaining emulsifying wax occurs simultaneous with atomizing the heat retaining skin treatment solution and overcomes a nozzle expansion cooling effect to allow the spray cloud to have a temperature of at least 15 degrees Fahrenheit above an ambient air temperature.

2. The method of claim 1, wherein air received from a supplemental air source associated with the sprayer is used in atomizing the heat retaining skin treatment solution.

3. The method of claim 1, further comprising heating the spray cloud using heated air emitted through a supplemental air outlet.

4. The method of claim 1, wherein the heat retaining emulsifying wax is phosphate based.

5. The method of claim 4, wherein the heat retaining emulsifying wax comprises a blend of fatty alcohol and phosphate esters.

6. The method of claim 1, wherein the heat retaining emulsifying wax comprises a blend of cetearyl alcohol and dicetyl phosphate.

7. The method of claim 1, wherein the heat retaining emulsifying wax comprises a blend of cetearyl alcohol and ceteth phosphate.

8. The method of claim 7, wherein the ceteth phosphate is ceteth-10 phosphate.

9. The method of claim 1 wherein the heat retaining skin treatment solution comprises silicone oil.

10. The method of claim 1, wherein the heat retaining skin treatment solution comprises dimethicone oil.

11. A system for applying a heated skin treatment spray to a target surface, comprising:
a heat retaining skin treatment solution comprising a heat retaining emulsifying wax;
a sprayer having an atomizing nozzle adapted to atomize the heat retaining skin treatment solution into a spray cloud;
a heating unit coupled to the sprayer and adapted to heat air, the air heating the heat retaining emulsifying wax; and
wherein heating the heat retaining emulsifying wax occurs simultaneously with atomizing the heat retaining skin treatment solution and overcomes a nozzle expansion cooling effect to allow the spray cloud to have a temperature of at least 85 degrees Fahrenheit.

12. The system of claim 11, further comprising a supplemental air source adapted to deliver the air to the sprayer.

13. The system of claim 11, further comprising a supplemental air outlet adapted to emit supplemental air to heat the spray cloud.

14. The system of claim 11, wherein the heat retaining emulsifying wax is phosphate based.

15. The system of claim 14, wherein the heat retaining emulsifying wax comprises a blend of fatty alcohol and phosphate esters.

16. The system of claim 11, wherein the heat retaining emulsifying wax comprises a blend of cetearyl alcohol and dicetyl phosphate.

17. The system of claim 11, wherein the heat retaining emulsifying wax comprises a blend of cetearyl alcohol and ceteth phosphate.

18. The system of claim 17, wherein the ceteth phosphate is ceteth-10 phosphate.

19. The system of claim 11, wherein the heat retaining skin treatment solution comprises silicone oil.

20. The system of claim 11, wherein the heat retaining skin treatment solution comprises dimethicone oil.

21. The system of claim 11, wherein the skin treatment solution comprises at least one of dihydroxyacetone and erythrulose.

22. The system of claim 11 wherein the atomizing nozzle comprises at least one atomization air port adapted to emit atomizing air to simultaneously heat and atomize the heat retaining skin treatment solution.

23. The system of claim 11 wherein the atomizing nozzle comprises at least one pattern shaping air port adapted to emit pattern shaping air to simultaneously heat and pattern shape the spray cloud.

24. The system of claim 11 wherein:
the atomizing nozzle is selected from a group consisting of: a mechanical atomizer, a sonic atomizer, and a hydraulic atomizer.

25. The system of claim 24 further comprising a supplemental air outlet, and supplemental air emitted from the supplemental air outlet heating the spray cloud.

26. The system of claim 11 wherein the heat retaining emulsifying wax is heated in a liquid conduit using the air approaching the atomizing nozzle.

27. The system of claim 11 wherein the heat retaining emulsifying wax is heated in a reservoir containing the heat retaining skin treatment solution.

28. The method of claim 1 further comprising heating the heat retaining emulsifying wax simultaneously with atomizing the heat retaining skin treatment solution using air emitted from at least one atomization air port associated with the atomizing nozzle.

29. The method of claim 1 further comprising heating the heat retaining emulsifying wax using air emitted from at least one pattern shaping port associated with the atomizing nozzle.

30. The method of claim 1 wherein:
the atomizing nozzle is selected from a group consisting of: a mechanical atomizer, a sonic atomizer, and a hydraulic atomizer.

31. The method of claim 30 further comprising heating the spray cloud using air emitted from a supplemental air outlet.

32. The method of claim 1 wherein the heat retaining emulsifying wax is heated in a liquid conduit using air approaching the atomizing nozzle.

33. The method of claim 1 wherein the heat retaining emulsifying wax is heated in a reservoir containing the heat retaining skin treatment solution.

34. A system for applying a heated skin treatment spray to a target surface, comprising:
a heat retaining skin treatment solution comprising a heat retaining emulsifying wax;
a sprayer having an atomizing nozzle including an air atomization port adapted to emit air to atomize the heat retaining skin treatment solution into a spray cloud; and
a heating unit coupled to the sprayer and adapted to heat the air, the air heating the heat retaining emulsifying wax simultaneously with atomizing the heat retaining skin treatment solution and overcoming a nozzle expansion cooling effect to allow the spray cloud to have a temperature of at least 85 degrees Fahrenheit.

35. The system of claim 34 wherein the heat retaining emulsifying wax is also heated in a liquid conduit using the air approaching the atomizing nozzle.

36. The system of claim 34 wherein the heat retaining emulsifying wax is also heated in a reservoir containing the heat retaining skin treatment solution.

37. The system of claim 11 wherein the temperature of the spray cloud is measured approximately five inches from the atomizing nozzle.

38. The system of claim 34 wherein the temperature of the spray cloud is measured approximately five inches from the atomizing nozzle.

\* \* \* \* \*